United States Patent
Birkhoff et al.

(10) Patent No.: US 9,796,644 B2
(45) Date of Patent: Oct. 24, 2017

(54) INTEGRATED PROCESS FOR PRODUCING CUMENE AND PURIFYING ISOPROPANOL

(75) Inventors: Ronald Birkhoff, Houston, TX (US); Raghavender Bhoomi, South Weymouth, MA (US)

(73) Assignee: BADGER LICENSING LLC, Boston, MA (US)

( * ) Notice: Subject to any disclaimer, the term of this patent is extended or adjusted under 35 U.S.C. 154(b) by 70 days.

(21) Appl. No.: 14/421,688

(22) PCT Filed: Aug. 14, 2012

(86) PCT No.: PCT/US2012/050750
§ 371 (c)(1),
(2), (4) Date: Feb. 18, 2015

(87) PCT Pub. No.: WO2014/028003
PCT Pub. Date: Feb. 20, 2014

(65) Prior Publication Data
US 2015/0218064 A1    Aug. 6, 2015

(51) Int. Cl.
*C07C 2/86* (2006.01)
*C07C 29/80* (2006.01)
*C07C 29/82* (2006.01)

(52) U.S. Cl.
CPC ............ *C07C 2/864* (2013.01); *C07C 29/80* (2013.01); *C07C 29/82* (2013.01); *Y02P 20/125* (2015.11)

(58) Field of Classification Search
CPC ............ C07C 2/864; C07C 29/80; C07C 2/86
See application file for complete search history.

(56) References Cited

U.S. PATENT DOCUMENTS

| | | | | |
|---|---|---|---|---|
| 3,031,384 A | * | 4/1962 | Sirois | .................. C07C 29/80 203/91 |
| 5,714,646 A | * | 2/1998 | Hirata | .................. C07C 29/04 203/28 |
| 6,512,153 B1 | | 1/2003 | Cappellazzo et al. | |
| 6,930,213 B1 | * | 8/2005 | Pompetzki | ............ C07C 29/145 568/881 |
| 2011/0178342 A1 | | 7/2011 | Hwang et al. | |

FOREIGN PATENT DOCUMENTS

SU        622801 A1    7/1978
WO    WO 2010042314 A1 *    4/2010    ............. C07C 2/864

OTHER PUBLICATIONS

International Search Report and Written Opinion issued in the corresponding PCT/US2012/050750 on May 17, 2013.

* cited by examiner

*Primary Examiner* — In Suk Bullock
*Assistant Examiner* — Youngsul Jeong
(74) *Attorney, Agent, or Firm* — Roberts Mlotkowski Safran Cole & Calderon P.C.

(57) ABSTRACT

An integrated process for producing cumene and purifying isopropanol is described, in which a crude isopropanol stream containing in excess of 0.1 wt % water is separated into a dry isopropanol fraction containing no more than 0.1 wt % water and a wet isopropanol fraction containing the remainder of the water in said crude isopropanol stream. The dry isopropanol fraction is recovered and the wet isopropanol fraction is contacted with benzene in an alkylation zone under alkylation conditions such that at least part of the isopropanol reacts with the benzene to produce an effluent stream comprising cumene.

13 Claims, No Drawings

INTEGRATED PROCESS FOR PRODUCING CUMENE AND PURIFYING ISOPROPANOL

CROSS-REFERENCE TO RELATED APPLICATIONS

The present application is a U.S. National Phase of PCT/US2012/050750 filed on Aug. 14, 2012. The disclosure of the PCT Application is hereby incorporated by reference into the present Application.

FIELD

This invention relates to an integrated process for producing cumene and purifying isopropanol.

BACKGROUND

Cumene is an important intermediate in the chemical and polymer industries, with global cumene production currently exceeding twelve million metric tons annually. The majority of all cumene manufactured in the world today is used for the production of phenol. The demand for phenol for the manufacture of Bisphenol-A and subsequently polycarbonates is accelerating, owing to the broadening application of polycarbonates in the electronic, healthcare, and automobile industries.

Commercial production of cumene generally involves the reaction of benzene with propylene under liquid phase or mixed gas-liquid phase conditions in the presence of an acid catalyst, particularly a zeolite catalyst. However, the demand for, and hence the cost of, propylene is increasing. There is therefore interest in developing alternative methods of producing cumene in which the propylene is replaced or supplemented by alternative $C_3$ alkylating agents. For example, U.S. Pat. No. 5,015,786 discloses a process in which acetone from a phenol plant is hydrogenated to produce isopropanol and the resultant isopropanol is then used as a $C_3$ alkylating agent in the liquid phase alkylation of benzene to cumene. This process has the added advantage that the production of phenol from cumene generates an equimolar amount of acetone, whereas the phenol and acetone are used at an approximately 2:1 molar ratio to produce Bisphenol-A. Thus, the process provides an attractive method of converting the excess acetone from phenol production to generation of the more advantaged product of cumene.

Isopropanol is not only useful as an alkylating agent for the production of cumene, but also enjoys wide application as a solvent, a gasoline additive and in various medical and pharmaceutical applications. On a commercial scale, isopropanol is produced either by acetone hydrogenation or via the direct or indirect hydration of propylene. However, each of these processes produces a crude isopropanol product containing significant quantities of water, whereas a key specification for industrial grade isopropanol is a water level of no more than 0.1 wt %. Removal of the water from the crude isopropanol product can be accomplished by fractionation or stripping, in conventional distillation systems, where water is removed as a light product and isopropanol product is produced as a heavy product with reduced water content. However, since water and isopropanol form a minimum boiling homogeneous azeotrope with a composition of approximately 80 wt % isopropanol and 20 wt % water, the initial water removal step results in an inevitable yield loss of isopropanol. Additional measures can be taken to reduce the isopropanol loss, such as the use of agents that either break the azeotrope, for example acetone, or form another azeotrope with water, such as benzene, or the use of solids adsorbents or selective membranes. However, all of these measures require additional equipment and processing steps, increasing the capital expenditure and operating cost, and hence increasing the cost to purify the isopropanol.

In accordance with the present invention, it has now been found that, by integrating the purification of isopropanol with a process for producing cumene from acetone, the purification of the crude isopropanol product can be simplified, thereby reducing production costs.

SUMMARY

In one aspect, the invention resides in an integrated process for producing cumene and purifying isopropanol, the process comprising:

(a) providing a crude isopropanol stream containing in excess of 0.1 wt % water;

(b) separating said crude isopropanol stream into a dry isopropanol fraction containing no more than 0.1 wt % water and a wet isopropanol fraction containing the remainder of the water in said crude isopropanol stream; and (c) contacting said wet isopropanol fraction with benzene in an alkylation zone under alkylation conditions such that at least part of the isopropanol reacts with the benzene to produce an effluent stream comprising cumene.

In one embodiment, the crude isopropanol stream is produced by the hydrogenation of acetone. Conveniently, the acetone is the by-product of a process for producing phenol from cumene, wherein at least part of the cumene is produced by the contacting (c).

In another embodiment, the crude isopropanol stream is produced by a process including hydration of propylene.

Typically, the crude isopropanol stream contains from 0.15 wt % to 3.0 wt % of water.

Generally, the separating (b) is effected by distillation or stripping.

Typically, the effluent stream produced in (c) further comprises water and unreacted benzene and the process further comprises:

(d) removing water from said effluent stream to produce a dried effluent stream; and (f) recycling at least a portion of the dried effluent stream to said contacting (c).

Conveniently, cumene is recovered from the effluent stream or the dried effluent stream before said portion of the dried effluent stream is recycled to said contacting (c).

DETAILED DESCRIPTION

A process is described for producing cumene from a crude isopropanol stream containing in excess of 0.1 wt % water, wherein the crude isopropanol stream is initially seaparated to allow removal of a dry isopropanol fraction which contains no more than 0.1 wt % water and which can be recovered for use as industrial grade isopropanol. The separation leaves a wet isopropanol fraction which contains the remainder of the water in the crude isopropanol stream and which can then be used as a $C_3$ alkylating agent in the alkylation of benzene to produce cumene. Thus, as will be described in more detail below, the present process integrates cumene production with the purification of crude isopropanol.

Crude Isopropanol Stream

The crude isopropanol stream employed in the present process contains in excess of 0.1 wt % water and normally from 0.15 wt % to 3.0 wt % of water. A suitable source of the crude isopropanol stream is the product of the direct or indirect hydration of propylene. More preferably, however, the crude isopropanol stream is produced by hydrogenation of excess acetone from a phenol plant, especially where the phenol is produced by the Hock process from cumene, which in turn is produced by reaction of benzene with $C_3$ alkylating agent including isopropanol and optionally propylene. The ensuing description will therefore focus on this preferred embodiment.

Purification of Crude Isopropanol Stream

The crude isopropanol stream can be separated into dry and wet isopropanol fractions by fractionation or stripping, in a conventional distillation system. Since water and isopropanol form a minimum boiling homogeneous azeotrope with a composition of approximately 80 wt % isopropanol and 20 wt % water, the dry isopropanol fraction can be removed as a heavy product, and the water is recovered as a light product along with isopropanol in the aforementioned azeoptropic composition. The dry isopropanol fraction contains no more than 0.1 wt % water, such as from 0 wt % to 0.05 wt % of water and can be recovered for use as industrial grade isopropanol. The wet isopropanol fraction typically contains from 10 wt % to 30 wt % of water and is fed to the benzene alkylation step.

Benzene Alkylation to Produce Cumene

In the benzene alkylation step, the wet isopropanol fraction, optionally together with additional $C_3$ alkylating agent, such as added propylene or added isopropanol, is reacted with benzene in the presence of a molecular sieve alkylation catalyst under conditions such that at least part of the benzene is maintained in the liquid phase during the process. Typical conditions include a temperature of about 20° C. to about 350° C., for example about 60° C. to about 300° C., a pressure of about 100 kPa to about 20,000 kPa, for example about 500 kPa to about 10,000 kPa, and a molar ratio of benzene to the $C_3$ alkylating agent of about 0.1:1 to about 100:1, such as about 1:1 to about 10:1. Where the $C_3$ alkylating agent contains propylene, the molar ratio of isopropanol to propylene is typically about 1 to 100 to about 100 to 1.

Generally, the alkylation is conducted in the presence of hydrogen, either added directly to the alkylation feed or present in the reactor effluent recycled from the acetone hydrogenation stage described below. Thus, it is found that hydrogen assists in removing the water coproduced with cumene in the alkylation step from the liquid phase reaction medium, thereby reducing the contact between the catalyst and the water and hence any tendency for the water to deactivate the catalyst. For some catalysts, the presence of hydrogen during the alkylation stage also reduces the deactivation caused by coke formation on the catalyst. Excessive hydrogen should, however, be avoided since it can lead to undesirable loss of benzene to cyclohexane. Conveniently, the molar ratio of hydrogen to isopropanol in said second reaction zone is about 0:1 to about 100:1, such as about 0:1 to about 10:1.

The catalyst employed in the alkylation step may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Alternatively, the alkylation catalyst may comprise one or more large pore molecular sieves having a Constraint Index less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferably, however, the alkylation catalyst comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation step may be carried out batchwise or on a continuous basis. Moreover, the reaction may be carried out in a fixed or moving bed reactor. Fixed bed operation is, however, preferred, typically with the alkylation reaction zone comprising one or a plurality of series-connected beds of alkylation catalyst.

The alkylation step is generally operated so as to achieve substantially complete conversion of the $C_3$ alkylating agent (isopropanol plus any added propylene) and hence the effluent from the alkylation reactor is composed mainly of cumene, coproduced water, water added with the wet isopropanol fraction, unreacted benzene, and reaction by-products, optionally together with hydrogen. Water is initially removed from the effluent by cooling the effluent and passing the cooled effluent to a decanter to separate the effluent into an aqueous phase and a water-depleted aromatic phase. An aliquot of the resultant aromatic phase is then separated and recycled to the alkylation zone in order to control the reaction temperature and to control the water content in the alkylation reactor. To accommodate the additional water that is sent to the alkylation step in the wet isopropanol fraction, adjustments to the process can be made to reduce the water content in the alkylation reaction, such as by reducing the temperature at which water separation is conducted and increasing the amount of the aromatic phase recycled to the alkylation reaction.

If hydrogen is present in the effluent, the cooled effluent is typically passed through a vapor/liquid separator before passage to the decanter. The vapor/liquid separator divides the cooled effluent into a hydrogen-rich vapor stream and a hydrogen-depleted liquid stream. The hydrogen-rich vapor stream can then be recycled to the alkylation reactor, generally after being compressed and cooled to separate any entrained water and aromatics. The hydrogen-depleted liquid stream is subsequently passed to the decanter for separation into the water-rich aqueous phase and the water-depleted aromatic phase.

After separation and recycle of an aliquot of the water-depleted aromatic phase, the remainder of the aromatic phase is passed to a distillation column, where the cumene is recovered and a benzene recycle stream containing unreacted benzene is separated for recycle back to the alkylation reaction zone.

Cumene Oxidation

The cumene recovered from the alkylation reaction effluent is converted to cumene hydroperoxide by a liquid phase oxidation process which is preferably carried out in a plurality of reactors connected in series. The oxidation process is conducted in the presence of an oxygen-containing gas, generally air, at a temperature from 50 to 120° C. and a pressure of 0 to 1 MPaG (gauge pressure). The total residence time in the oxidation reactors is usually from 3 to 20 hours.

The oxidation reaction may be carried out with or without a catalyst. Where a catalyst is employed, suitable catalysts include basic materials, such as carbonate and hydroxide compounds of alkali metals, such as lithium, sodium and potassium, and alkaline earth metals such as calcium and magnesium. These compounds may be used in solid form or in aqueous solution. The amount of catalyst (metal basis) is usually not more than 10 g equivalent, preferably 0.1 to 6 g equivalent per 1 ton of cumene.

The product of the oxidation reaction comprises a gas phase composed of spent air containing entrained cumene and a liquid phase which generally comprises 20 to 50% by weight of cumene hydroperoxide and 50 to 80% by weight of unreacted cumene, together with various by-products mainly composed of dimethyl phenyl carbinol (DMPC).

The gas phase product from the oxidation stage is cooled and then passed through a series of adsorbent beds, normally comprising charcoal, where the entrained cumene is removed before the spent air is vented to atmosphere or flared. The cumene collected by the charcoal adsorbers is recovered by desorption with low-pressure steam followed by condensation of the steam and decanting of the organic and water phases. The organic phase is then fed to a cumene recycle system described in more detail below.

The liquid phase product from the oxidation stage is heated in one or more stages, typically under vacuum, to remove most of the unreacted cumene and concentrate the cumene hydroperoxide in the product to 75 to 85 wt % before the product is fed to the cleavage step. The cumene vapor removed from the liquid phase product is cooled and combined with other cumene recycle streams produced in the process, such as the cumene recovered from the spent air, before being sent to the cumene recycle system.

Cumene Hydroperoxide Cleavage

The concentrated cumene hydroperoxide from the oxidation stage is decomposed or cleaved in a backmixed reactor in the presence of an acid catalyst, normally sulfuric acid, mainly to phenol and acetone, while most of the DMPC by-product is converted to α-methylstyrene (AMS). The cleavage reaction is typically carried out at a temperature of about 40° C. to about 60° C. and a pressure of about 0 kPa to about 500 kPa.

The acid catalyst added to the cleavage reactor must be neutralized to prevent yield loss due to side reactions and to protect against corrosion in the downstream fractionation section. This is typically achieved by injecting caustic into the cleavage reactor effluent before the effluent passes to the fractionation section.

After neutralization, the cleavage effluent is initially passed to an acetone recovery section comprising at least a crude acetone recovery column and a finished acetone recovery column. In the crude acetone recovery column, the effluent is separated into a crude phenol bottoms stream, which is fed to a phenol recovery section, and a crude acetone overhead stream. The overhead stream is then fed to the finished acetone recovery column, where unreacted cumene and water are removed as a bottoms stream and acetone product is recovered as an overhead stream. After removal of the water, the unreacted cumene is sent to the cumene recycle system.

The crude phenol stream removed in the acetone recovery section is fed to a phenol recovery section which again comprises a multi-column distillation section, where a mixed cumene/AMS stream is removed before the crude phenol undergoes various chemical treatments and fractionation before a finished phenol product is recovered.

The mixed cumene/AMS stream removed in the phenol recovery section is initially subjected to a caustic wash to remove any residual acid and is then passed to a hydrogenation reactor where the AMS undergoes mild hydrogenation in the presence of a platinum catalyst to produce cumene with high selectivity. The resultant cumene enriched product is then sent to the cumene recycle system.

The cumene recycle system returns the unreacted and produced cumene generated in the process back to the cumene oxidation step.

Acetone Hydrogenation

Generally, the phenol and acetone recovered from the cleavage effluent are used in a molar ratio of 2:1 to produce Bisphenol A, thereby resulting in a net surplus of acetone. In the present process, the excess acetone from the cleavage stage is hydrogenated to produce isopropanol for recycle to alkylation stage. The acetone hydrogenation is effected by contacting the excess acetone with hydrogen in the presence of a metal-containing catalyst. Generally the catalyst is Raney nickel, but other useful catalysts include nickel, copper-chromium, Raney nickel-copper, copper-zinc and platinum group metals, for example, platinum, palladium, ruthenium, rhodium, and similar metals on active carbon, aluminum and other carriers. The reaction temperature may range from 20° C. to about 350° C., but more generally is between about 40° C. and 250° C., such as between about 60° C. and 200° C. The hydrogenation may be carried out by either liquid, gas, or mixed gas-liquid phase reaction. The pressure may range from 100 kPa to 20,000 kPa, such as from about 500 to about 10,000 kPa. The hydrogen gas is generally present in a molar ratio relative to the acetone reactant of from 0.1:1 to 100:1, such as from 1:1 to 10:1.

The hydrogenation may be carried out in the presence or absence of a reaction medium. Examples of suitable media include alcohols such as methanol, ethanol, propanol, and butanol. Also useful is isopropanol which is a hydrogenation product of acetone. Also useful are glycols such as ethylene glycol, propylene glycol, diethylene glycol, and triethylene glycol; and ethers such as diisopropyl ether, dibutyl ether, ethylene glycol dimethyl ether, diglyme (diethylene glycol dimethyl ether) and triglyme. Aprotic polar solvents may also be used, for example, dimethylformamide, dimethylacetamide, acetonitrile, and dimethyl sulfoxide. Also useful are saturated hydrocarbons such as hexane, heptane, cyclopentane, and cyclohexane. Water can also be used as a solvent in the hydrogenation reaction.

The hydrogenation step may be carried out batchwise or on a continuous basis. Depending on the shape of a particular catalyst used, the reaction may be carried out in a fluidized bed using powder catalyst or a fixed bed using granular catalyst. Fixed bed operation is preferred in view of ease of separation of the catalyst from the reaction mixture and simplicity of the reaction system.

The hydrogenation reaction is exothermic and, to avoid excessive temperature rise, part of the reaction effluent, composed mainly of isopropanol, can be cooled and recycled to hydrogenation reactor inlet. In one embodiment, the weight ratio of liquid recycle to acetone feed is between about 1:1 and about 100:1.

In addition, part of the unreacted hydrogen in the hydrogenation reaction effluent can be recycled to the hydrogenation reactor inlet so as to reduce the level of hydrogen in the isopropanol-containing feed to the alkylation step.

The invention claimed is:

1. An integrated process for producing cumene and purifying isopropanol, the process comprising:
   (a) providing a crude isopropanol stream containing in excess of 0.1 wt % water;
   (b) separating said crude isopropanol stream into a dry isopropanol fraction containing no more than 0.1 wt % water and a wet isopropanol fraction containing the remainder of the water in said crude isopropanol stream; and
   (c) contacting said wet isopropanol fraction with benzene in an alkylation zone under alkylation conditions such that at least part of the isopropanol reacts with the benzene to produce an effluent stream comprising cumene.

2. The process of claim 1, wherein said crude isopropanol stream is produced by hydrogenation of acetone.

3. The process of claim 2, wherein said acetone is the by-product of a process for producing phenol from cumene.

4. The process of claim 3, wherein at least part of the cumene is produced by said contacting (c).

5. The process of claim 1, wherein said crude isopropanol stream is produced by a process including hydration of propylene.

6. The process of claim 1, wherein said crude isopropanol stream contains from 0.15 wt % to 3.0 wt % of water.

7. The process of claim 1, wherein said separating (b) is effected by distillation or stripping.

8. The process of claim 1, wherein said contacting takes place in the presence of a molecular sieve alkylation catalyst.

9. The process of claim 8, wherein said molecular sieve alkylation catalyst comprises at least one zeolite catalyst selected from the group comprising ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8.

10. The process of claim 8, wherein said molecular sieve alkylation catalyst comprises at least one zeolite catalyst selected from the group comprising MCM-22, PSH-3, SSZ-25, ERB-1, ITQ-1, ITQ-2, MCM-36, MCM-49, MCM-56, UZM-8, and mixtures thereof.

11. The process of claim 1, wherein said alkylation conditions comprise a temperature of 20° C. to 350° C., a pressure of 100 kPa to 20,000 kPa, and a molar ratio of benzene to $C_3$ alkylating agent (including isopropanol) fed to said alkylation zone of 0.1:1 to 100:1.

12. The process of claim 1, wherein the effluent stream produced in (c) further comprises water and unreacted benzene and the process further comprises:

(d) removing water from said effluent stream to produce a dried effluent stream; and (f) recycling at least a portion of the dried effluent stream to said contacting (c).

13. The process of claim 12, wherein cumene is recovered from said effluent stream or said dried effluent stream before said portion of the dried effluent stream is recycled to said contacting (c).

* * * * *